US009274085B2

(12) United States Patent
Endo et al.

(10) Patent No.: US 9,274,085 B2
(45) Date of Patent: Mar. 1, 2016

(54) EDDY CURRENT INSPECTION DEVICE, EDDY CURRENT INSPECTION PROBE, AND EDDY CURRENT INSPECTION METHOD

(71) Applicant: Hitachi, Ltd., Chiyoda-ku, Tokyo (JP)

(72) Inventors: Hisashi Endo, Hitachi (JP); Akira Nishimizu, Tokai (JP); Noriyuki Sadaoka, Tokai (JP)

(73) Assignee: Hitachi, Ltd., Tokyo (JP)

( * ) Notice: Subject to any disclaimer, the term of this patent is extended or adjusted under 35 U.S.C. 154(b) by 93 days.

(21) Appl. No.: 13/787,953

(22) Filed: Mar. 7, 2013

(65) Prior Publication Data

US 2013/0241541 A1    Sep. 19, 2013

(30) Foreign Application Priority Data

Mar. 19, 2012   (JP) .................................. 2012-061918

(51) Int. Cl.
*G01N 27/87*   (2006.01)
*G01N 27/90*   (2006.01)
*G01R 33/385*   (2006.01)

(52) U.S. Cl.
CPC .............. *G01N 27/87* (2013.01); *G01N 27/902* (2013.01); *G01R 33/385* (2013.01)

(58) Field of Classification Search
CPC ....... G01N 27/87; G01N 27/72; G01N 27/82; G01R 33/0035; G01R 35/005; G01R 33/0023; G01R 33/0283; G01R 33/422; G01R 33/56518
USPC ......... 324/219, 220, 221, 228–243, 260, 261, 324/202, 225; 702/38
See application file for complete search history.

(56) References Cited

U.S. PATENT DOCUMENTS 4,649,343 A    3/1987   Birchak et al.
6,636,037 B1 *  10/2003  Ou-Yang ....................... 324/240
(Continued)

FOREIGN PATENT DOCUMENTS

JP    62-172259 A    7/1987
JP    5-99901 A    4/1993
(Continued)

OTHER PUBLICATIONS

European Search Report Dated Jul. 30, 2013 {Six (6) Pages}.
(Continued)

*Primary Examiner* — Alesa Allgood
(74) *Attorney, Agent, or Firm* — Crowell & Moring LLP

(57) ABSTRACT

Provided is an eddy current inspection device, an eddy current inspection probe and an eddy current inspection method that make it possible to detect defects existing in deeper parts of test objects. Three or more odd number of excitation coils are arranged at even intervals in a circumferential direction on a postulated circumference. Excitation currents applied to the excitation coils are controlled so that the phase difference between excitation currents applied to adjacent ones of the excitation coils arranged in the circumferential direction on the postulated circumference equals one cycle divided by the number of excitation coils. A magnetic field generated according to an eddy current occurring in the test object due to a magnetic field caused by the application of the excitation currents to the excitation coils is detected by use of a detector arranged on a postulated plane containing the postulated circumference but inside the postulated circumference.

3 Claims, 14 Drawing Sheets

(56) References Cited

U.S. PATENT DOCUMENTS

| | | | |
|---|---|---|---|
| 2004/0189585 A1* | 9/2004 | Moon | 345/100 |
| 2005/0237055 A1* | 10/2005 | Sun et al. | 324/240 |
| 2012/0092005 A1* | 4/2012 | Hibino et al. | 324/242 |

FOREIGN PATENT DOCUMENTS

| JP | 10-197493 A | 7/1998 |
|---|---|---|
| JP | 2000-9696 A | 1/2000 |
| JP | 2009-257794 A | 11/2009 |
| JP | 2011-7780 A | 1/2011 |

OTHER PUBLICATIONS

Japanese-language Office Action issued in counterpart Japanese Application No. 2012-061918 dated Sep. 1, 2015 (Three (3) pages).

* cited by examiner

EDDY CURRENT INSPECTION DEVICE, EDDY CURRENT INSPECTION PROBE, AND EDDY CURRENT INSPECTION METHOD

BACKGROUND OF THE INVENTION

1. Field of the Invention

The present invention relates to an eddy current inspection device, an eddy current inspection probe and an eddy current inspection method for detecting a characteristic change of an inspection target (test object) such as a flaw or a change in material quality occurring on the surface or inside of the inspection target.

2. Description of the Related Art

The eddy current inspection method involves detecting a characteristic change such as a flaw or a change in material quality (hereinafter referred to as a "defect") occurring on the surface or inside of the test object by measuring a change in an eddy current caused in the test object by time-varying magnetic fluxes. The time-varying magnetic fluxes are generated by use of an excitation coil placed in the vicinity of the surface of the test object by applying time-varying electric current (excitation current) to the excitation coil.

Conventional techniques employing the eddy current inspection method include, for example, a technique disclosed in JP-05-99901-A in regard to an eddy current inspection device. The eddy current inspection device according to JP-05-99901-A comprises a plurality of excitation coils, rotational magnetic field generating means, a plurality of detection coils, and flaw detection means. The excitation coils are attached to a magnetic core and arranged at fixed angular intervals for the purpose of detecting the presence/absence of a defect and the direction of each defect in a flat metal plate, etc. The rotational magnetic field generating means magnetically excites the excitation coils with a signal generated by amplitude modulation by use of AC voltage and thereby applies a rotational magnetic field to the test object. The detection coils are arranged on the magnetic core corresponding to the excitation coils in order to detect a magnetic field generated from the test object according to an eddy current occurring in the test object. The flaw detection means detects defects existing in the test object based on output signals from the detection coils.

SUMMARY OF THE INVENTION

However, defects in the test object can develop not only at the surface of the test object or in the vicinity of the surface but also in a deeper part. Therefore, defect inspection in deeper parts of test objects is being required in order to further improve the reliability of the defect inspection of test objects.

The eddy current in the test object caused by the magnetic fluxes from the excitation coils has a tendency to develop to a deeper part of the test object with the decrease in the frequency of the excitation currents. However, there exists the problem that the magnetic field information acquired from the deep part of the test object is far more deficient compared to the magnetic field information from around the surface of the test object even at still lower frequencies. Therefore, the defect inspection in deep parts of test objects has been extremely difficult.

The object of the present invention, which has been made in consideration of the above situation, is to provide an eddy current inspection device, an eddy current inspection probe and an eddy current inspection method that make it possible to detect defects existing in deeper parts of test objects.

(1) To achieve the above object, the present invention provides an eddy current inspection device comprising: a main unit which has a function of generating and outputting a fundamental signal as the foundation for generating excitation currents to be used for inspection of a test object; an eddy current inspection probe which is provided separately from the main unit to be able to scan the test object while moving along the surface of the test object, the eddy current inspection probe including three or more odd number of excitation coils which are arranged at even intervals in a circumferential direction on a postulated circumference to be excited by the excitation currents applied thereto and a detector which is arranged on a postulated plane containing the postulated circumference but inside the postulated circumference to detect a magnetic field generated according to an eddy current occurring in the test object due to a magnetic field caused by the application of the excitation currents to the excitation coils; and excitation current generating means which generates the excitation currents based on the fundamental signal so that the phase difference between excitation currents applied to adjacent ones of the excitation coils arranged in the circumferential direction on the postulated circumference in the eddy current inspection probe equals one cycle divided by the number of excitation coils.

(2) Preferably, in the above eddy current inspection device (1), the excitation current generating means is provided integrally with the main unit.

(3) Preferably, in the above eddy current inspection device (1), the excitation current generating means is provided integrally with the eddy current inspection probe.

(4) Preferably, in the above eddy current inspection device (1), the excitation current generating means is provided separately from the main unit or the eddy current inspection probe.

(5) Preferably, in the above eddy current inspection device (1), the detector of the eddy current inspection probe is arranged at the center of the postulated circumference.

(6) Preferably, in the above eddy current inspection device (1), the detector of the eddy current inspection probe is arranged at a position shifted from the center of the postulated circumference.

(7) To achieve the above object, the present invention provides an eddy current inspection probe comprising: a detection function unit including three or more odd number of excitation coils which are arranged at even intervals in a circumferential direction on a postulated circumference to be excited by excitation currents applied thereto and a detector which is arranged on a postulated plane containing the postulated circumference but inside the postulated circumference to detect a magnetic field generated according to an eddy current occurring in a test object due to a magnetic field caused by the application of the excitation currents to the excitation coils; and excitation current generating means which generates the excitation currents based on a fundamental signal supplied from a main unit having a function of outputting the fundamental signal as the foundation for generating the excitation currents to be used for inspection of the test object, the excitation current generating means generating the excitation currents so that the phase difference between excitation currents applied to adjacent ones of the excitation coils arranged in the circumferential direction on the postulated circumference in the eddy current inspection probe equals one cycle divided by the number of excitation coils.

(8) To achieve the above object, the present invention provides an eddy current inspection probe comprising a detection function unit. The detection function unit includes: three or more odd number of excitation coils which are arranged at even intervals in a circumferential direction on a postulated circumference to be excited by excitation currents applied thereto; and a detector which is arranged on a postulated plane containing the postulated circumference but inside the postulated circumference to detect a magnetic field generated according to an eddy current occurring in a test object due to a magnetic field caused by the application of the excitation currents to the excitation coils. The excitation coils are supplied with excitation currents generated so that the phase difference between excitation currents applied to adjacent ones of the excitation coils arranged in the circumferential direction on the postulated circumference in the eddy current inspection probe equals one cycle divided by the number of excitation coils based on a fundamental signal supplied from a main unit having a function of outputting the fundamental signal as the foundation for generating the excitation currents to be used for inspection of the test object.

(9) Preferably, in the above eddy current inspection device (7) or (8), the detector is arranged at the center of the postulated circumference.

(10) Preferably, in the above eddy current inspection device (7) or (8), the detector is arranged at a position shifted from the center of the postulated circumference.

(11) To achieve the above object, the present invention provides an eddy current inspection method comprising the steps of: generating excitation currents for three or more odd number of excitation coils arranged at even intervals in a circumferential direction on a postulated circumference so that the phase difference between excitation currents applied to adjacent ones of the excitation coils arranged in the circumferential direction on the postulated circumference equals one cycle divided by the number of excitation coils; applying the generated excitation currents to the excitation coils; and detecting a magnetic field generated according to an eddy current occurring in a test object due to a magnetic field caused by the application of the excitation currents to the excitation coils by use of a detector arranged on a postulated plane containing the postulated circumference but inside the postulated circumference.

According to the present invention, defects existing in deeper parts of test objects can be detected.

DESCRIPTION OF THE PREFERRED EMBODIMENTS

Figure 1:
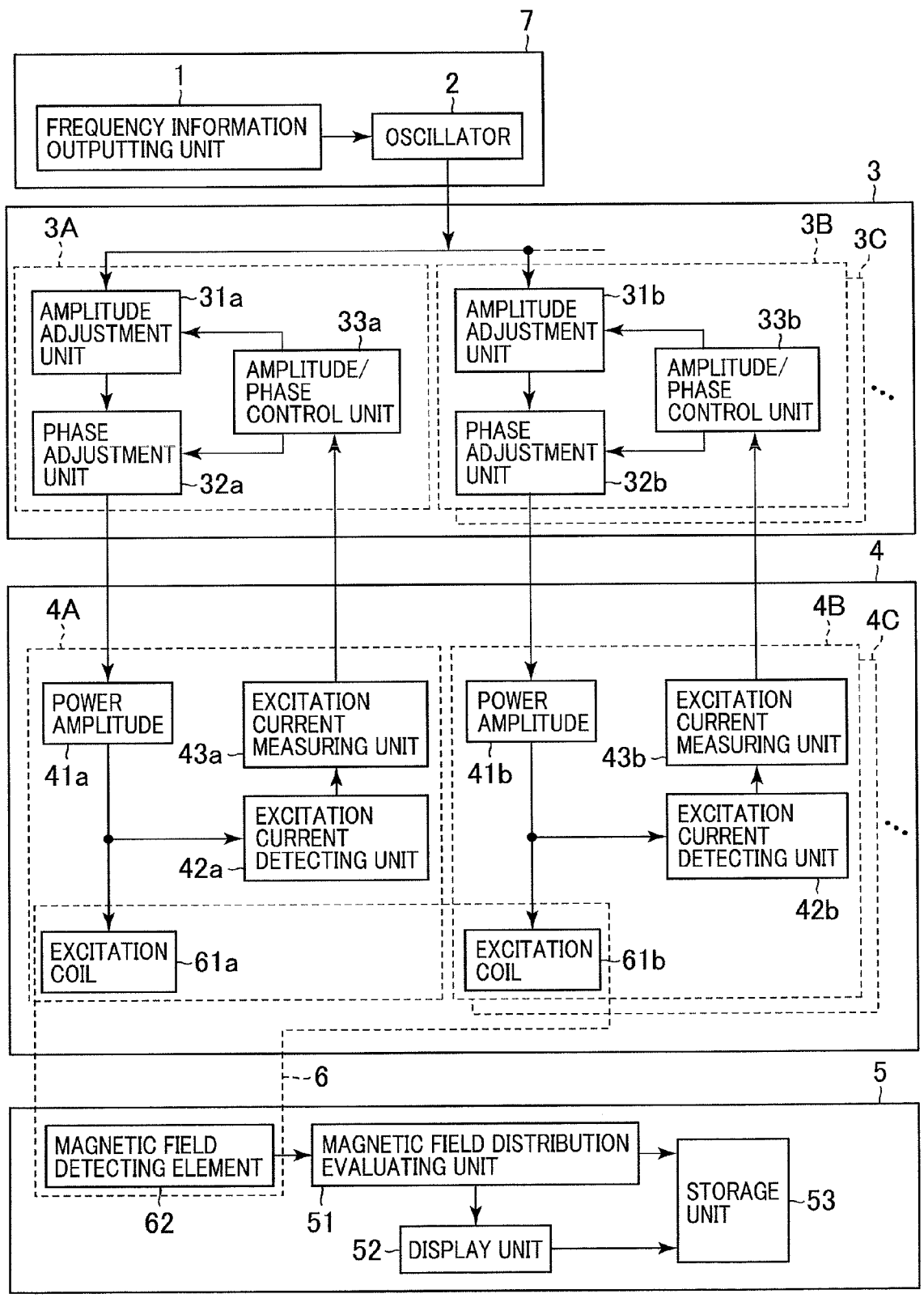
FIG. 1 is a functional block diagram showing the outline of the overall configuration of an eddy current inspection device in accordance with a first embodiment of the present invention.

Referring now to the drawings, a description will be given in detail of preferred embodiments in accordance with the present invention.

First Embodiment

Figure 2:
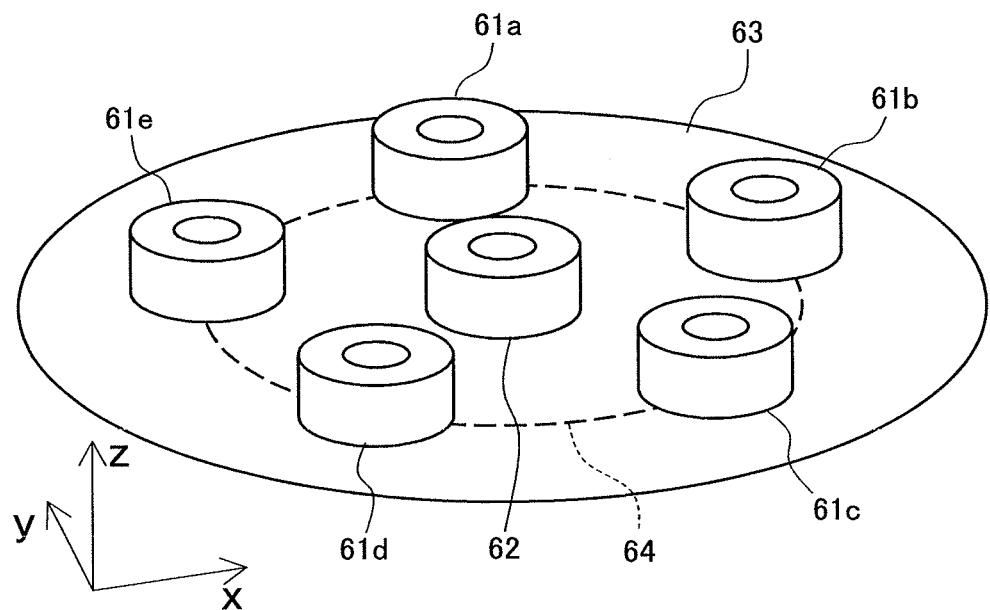
FIG. 2 is a perspective view schematically showing the arrangement of excitation coils and a detection coil in an eddy current inspection probe of the eddy current inspection device.
Figure 3:
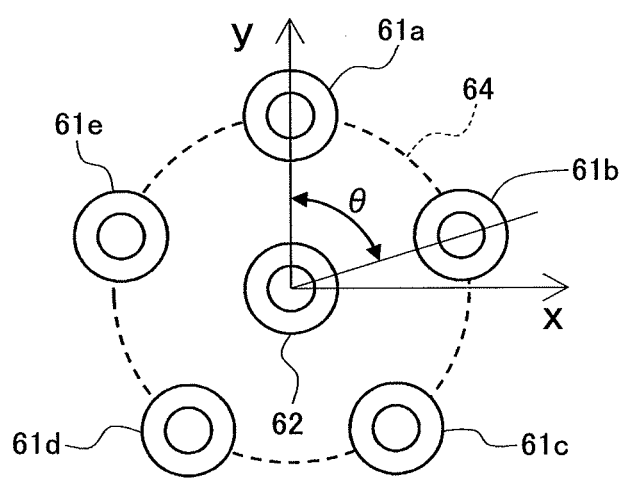
FIG. 3 is a plan view schematically showing the arrangement of the excitation coils and the detection coil in the eddy current inspection probe of the eddy current inspection device.

FIG. 1 is a functional block diagram showing the outline of the overall configuration of an eddy current inspection device in accordance with the first embodiment of the present invention. FIGS. 2 and 3 are a perspective view and a plan view schematically showing the arrangement of excitation coils and a detection coil in an eddy current inspection probe of the eddy current inspection device.

Referring to FIG. 1, the eddy current inspection device of this embodiment comprises a frequency information outputting unit 1, a fundamental signal generating section 7, an excitation signal generating section 3, a magnetic field generating section 4 and a detection section 5. The frequency information outputting unit 1 generates and outputs information on the frequency of a fundamental signal. The fundamental signal generating section 7 has an oscillator 2 for generating and outputting the fundamental signal (as the foundation for generating excitation currents to be used for the inspection of the test object) based on the frequency information supplied from the frequency information outputting unit 1. The excitation signal generating section 3 generates and outputs excitation signals based on the fundamental signal supplied from the oscillator 2. The magnetic field generating section 4 generates a magnetic field to be used for the inspection according to the excitation signals supplied from the excitation signal generating section 3. The detection section 5 detects a magnetic field generated according to an eddy current occurring in the test object due to the magnetic field generated by the magnetic field generating section 4.

The excitation signal generating section 3 includes a plurality of excitation signal generating units 3A-3C, . . . for respectively generating excitation signals corresponding to a plurality of (five in this embodiment) excitation coils 61a-61e (see FIGS. 2 and 3) based on the fundamental signal supplied from the oscillator 2. Among the signal generating units 3A-3C, . . . , only those corresponding to the excitation coils 61a-61c are shown in FIG. 1 as representatives.

The excitation signal generating unit 3A includes an amplitude adjustment unit 31a which adjusts the amplitude of the fundamental signal supplied from the oscillator 2, a phase adjustment unit 32a which adjusts the phase of the fundamental signal and outputs the adjusted signal as the excitation signal, and an amplitude/phase control unit 33a which controls the operation of the amplitude adjustment unit 31a and the phase adjustment unit 32a based on a measurement result inputted from an excitation current measuring unit 43a which will be explained later.

The other excitation signal generating units 3B, 3C, . . . also have equivalent configurations. Specifically, each excitation signal generating unit 3B, 3C, . . . includes an amplitude adjustment unit 31b, 31c, . . . which adjusts the amplitude of the fundamental signal supplied from the oscillator 2, a phase adjustment unit 32b, 32c, . . . which adjusts the phase of the fundamental signal and outputs the adjusted signal as the excitation signal, and an amplitude/phase control unit 33b, 33c, . . . which controls the operation of the amplitude adjustment unit 31b, 31c, . . . and the phase adjustment unit 32b, 32c, . . . based on an excitation current measurement result inputted from an excitation current measuring unit 43b, 43c, . . . which will be explained later.

The magnetic field generating section 4 includes a plurality of magnetic field generating units 4A-4C, . . . for respectively generating magnetic fields according to the excitation signals supplied from the excitation signal generating units 3A-3C, . . . of the excitation signal generating section 3. Among the magnetic field generating units 4A-4C, . . . only those corresponding to the excitation coils 61a-61c are shown in FIG. 1 as representatives.

The magnetic field generating unit 4A includes the excitation coil 61a, a power amplifier 41a, an excitation current detecting unit 42a, and an excitation current measuring unit 43a. The power amplifier 41a amplifies the electric power of the excitation signal supplied from the excitation signal generating unit 3A and applies the amplified electric power to the excitation coil 61a as the excitation current. The excitation coil 61a generates a magnetic field according to the excitation current supplied thereto. The excitation current detecting unit 42a detects the amplitude component and the phase component of the excitation current applied by the power amplifier 41a to the excitation coil 61a. The excitation current measuring unit 43a measures the amplitude and the phase of the excitation current based on the result of the detection by the excitation current detecting unit 42a and outputs the excitation current measurement result to the amplitude/phase control unit 33a of the excitation signal generating unit 3A.

The other magnetic field generating units 4B, 4C, . . . also have equivalent configurations. Specifically, each magnetic field generating unit 4B, 4C, . . . includes an excitation coil 61b, 61c . . . which generates a magnetic field according to the excitation current supplied thereto, a power amplifier 41b, 41c, . . . which amplifies the electric power of the excitation signal supplied from the excitation signal generating unit 3B, 3C, . . . and applies the amplified electric power to the excitation coil 61b, 61c, . . . as the excitation current, an excitation current detecting unit 42b, 42c, . . . which detects the amplitude component and the phase component of the excitation current applied by the power amplifier 41b, 41c, . . . to the excitation coil 61b, 61c, . . . and an excitation current measuring unit 43b, 43c, . . . which measures the amplitude and the phase of the excitation current based on the result of the detection by the excitation current detecting unit 42b, 42c, . . . and outputs the excitation current measurement result to the amplitude/phase control unit 33b, 33c, . . . of the excitation signal generating unit 3B, 3C, . . . .

The detection section 5 includes a magnetic field detecting element 62, a magnetic field distribution evaluating unit 51, a display unit 52, and a storage unit 53. The magnetic field detecting element 62 (implemented by a detection coil in this embodiment) serves as a detector for detecting the magnetic field generated according to the eddy current occurring in the test object due to the magnetic field caused by the application of the excitation currents to the excitation coils 61a-61c, . . . . The magnetic field distribution evaluating unit 51 extracts a change in the magnetic field distribution caused by a characteristic change such as a flaw or a change in material quality occurring on the surface or inside of the test object (hereinafter referred to as a "defect") based on the result of the detection by the magnetic field detecting element 62. The display unit 52 displays the result of the extraction by the magnetic field distribution evaluating unit 51. The storage unit 53 stores the result of the extraction by the magnetic field distribution evaluating unit 51.

Incidentally, while the coil having the property of increasing the level of the detected signal (output voltage) with the increase in the sharpness of the change in the magnetic field as the target of detection (i.e., with the increase in the amount of change of the magnetic field per unit time) is employed as an example of the magnetic field detecting element 62 in this embodiment, other types of sensors directly converting the strength of the magnetic field into the output voltage may also be employed in place of the coil. The employable sensors include a Hall sensor, an MI (Magneto-Impedance) sensor, a GMR (Giant Magneto-Resistive) sensor, an AMR (Anisotropic Magneto-Resistance) sensor, a TMR (Tunnel Magneto-Resistance) sensor, an FG (Flux Gate) sensor, a SQUID (Superconducting Quantum Interference Device) sensor, etc.

In the configuration described above, the excitation signal generating section 3 and the power amplifiers 41a-41c, ... the excitation current detecting units 42a-42c, ... and the excitation current measuring units 43a-43c, ... of the magnetic field generating section 4 form an excitation current generating section which generates the excitation currents according to the fundamental signal. The excitation current generating section, the fundamental signal generating section 7 and the magnetic field distribution evaluating unit 51, the display unit 52 and the storage unit 53 of the detection section 5 form a main unit. The excitation coils 61a-61c, ... and the magnetic field detecting element 62 form an eddy current inspection probe 6 which is provided separately from the main unit to be able to scan the test object while moving along the surface of the test object.

Referring to FIG. 2, the eddy current inspection probe 6 according to this embodiment includes three or more odd number of (five in this embodiment) excitation coils 61a-61e and the detection coil 62. The excitation coils 61a-61e are arranged at even intervals in the circumferential direction on a postulated circumference 64 to be excited by the application of the excitation currents. The detection coil 62 is arranged on a postulated plane 63 containing the postulated circumference 64 but inside the postulated circumference 64 to serve as the detector for detecting the magnetic field generated according to the eddy current occurring in the test object due to the magnetic field caused by the application of the excitation currents to the excitation coils 61a-61e.

FIG. 2 shows a case where five excitation coils 61a-61e are arranged at even intervals in the circumferential direction on the postulated circumference 64 and the detection coil 62 is arranged at the center of the postulated circumference 64 on the postulated plane 63. Thus, the excitation coils 61a-61e are arranged at equal distances from the center of the postulated circumference 64 and at even angles θ=360 (degrees)÷5 (pieces)=72 (degrees) around the center. Incidentally, when the number of excitation coils is three, the angle between adjacent excitation coils is θ=120 (degrees). The angle is θ=51.4 (degrees) when the number of excitation coils is seven, and θ=40 (degrees) when the number of excitation coils is nine.

Figure 4:
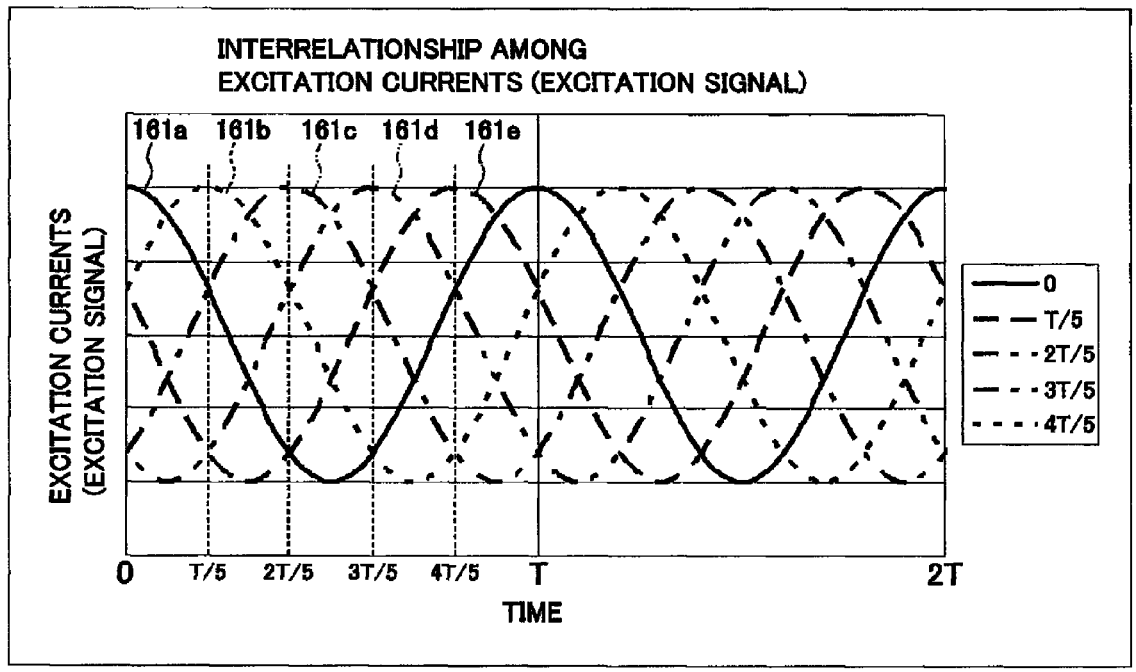
FIG. 4 is a graph showing the interrelationship among excitation currents respectively applied to the excitation coils of the eddy current inspection probe.

FIG. 4 is a graph showing the interrelationship among the excitation currents applied to the excitation coils 61a-61e of the eddy current inspection probe 6. The excitation signals supplied from the excitation signal generating section 3 to the power amplifiers 41a, 41b, ... of the magnetic field generating section 4 are also in the same interrelationship. In FIG. 4, the vertical axis represents the amplitude of each excitation current (or each excitation signal) and the horizontal axis represents the time. Explanation of the absolute values of the excitation currents applied to the excitation coils 61a-61e (or the excitation signals) is omitted here since the graph of FIG. 4 simply illustrates the interrelationship among the excitation currents (or among the excitation signals).

As shown in FIG. 4, excitation currents 161a-161e are applied to the excitation coils 61a-61e, respectively. Specifically, excitation currents 161a-161e that have been controlled so that the phase difference between adjacent excitation currents (applied to adjacent ones of the excitation coils 61a-61e arranged in the circumferential direction on the postulated circumference 64) equals one cycle divided by the number (5 in this example) of excitation coils 61a-61e (T/5 in this example) are applied to the excitation coils 61a-61e of the eddy current inspection probe 6.

For example, assuming that the cycle of the excitation current 161a applied to the excitation coil 61a equals T, the excitation current 161b for the excitation coil 61b also has the same cycle T and is applied to the excitation coil 61b one fifth of the cycle (T/5) later than the excitation current 161a. Similarly, the excitation currents 161c, 161d and 161e for the excitation coils 61c, 61d and 61e also have the same cycle T and are applied T/5 later than the excitation currents 161b, 161c and 161d, respectively. In the same sense, the excitation current 161a for the excitation coil 61a is applied T/5 later than the excitation current 161e.

To sum up, when the number of excitation coils is N (arbitrary number), each excitation current for each one of the excitation coils has the same cycle T and is applied 1/N of the cycle (T/N) later than the adjacent excitation current applied to the adjacent excitation coil on the postulated circumference 64.

FIGS. 5-12 are schematic diagrams showing the directions and the intensities of the magnetic field generated by the eddy current inspection probe 6, wherein FIGS. 5-8 are top views and FIGS. 9-12 are perspective views. In the figures, the direction of the magnetic field at each position is indicated by the direction of each arrow, and the intensity of the magnetic field at each position is indicated by the darkness of each arrow. Each arrow represents a stronger/weaker magnetic field with the increase/decrease in the darkness (i.e., with the increase in the blackness/whiteness).

Figure 5:
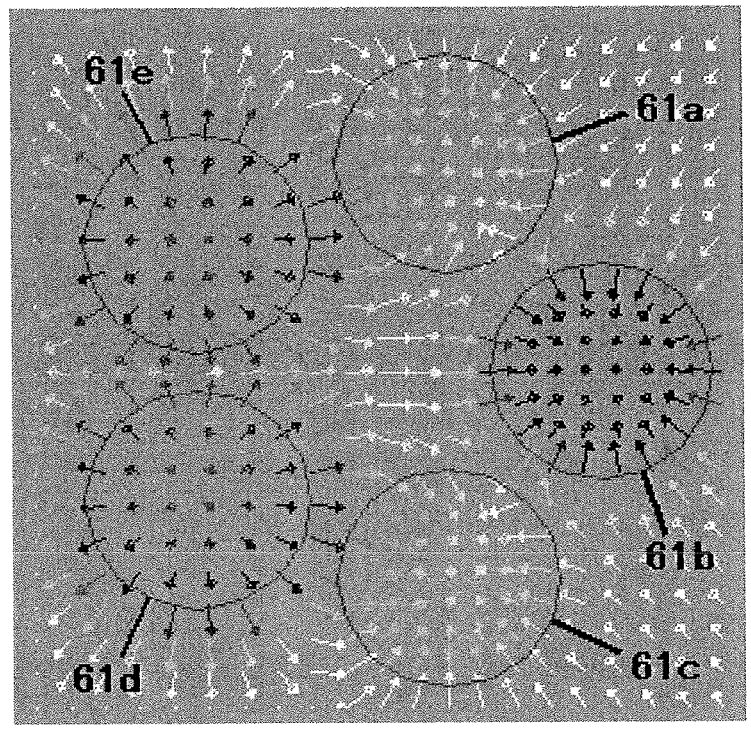
FIG. 5 is a top view showing the directions and the intensities of a magnetic field generated by the eddy current inspection probe at time 0.
Figure 6:
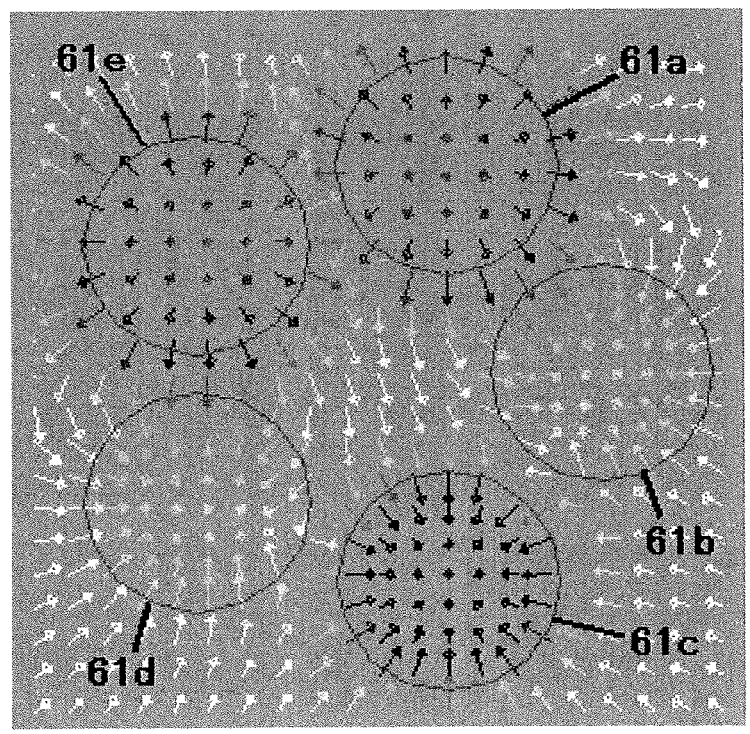
FIG. 6 is a top view showing the directions and the intensities of the magnetic field generated by the eddy current inspection probe at time T/6.
Figure 7:
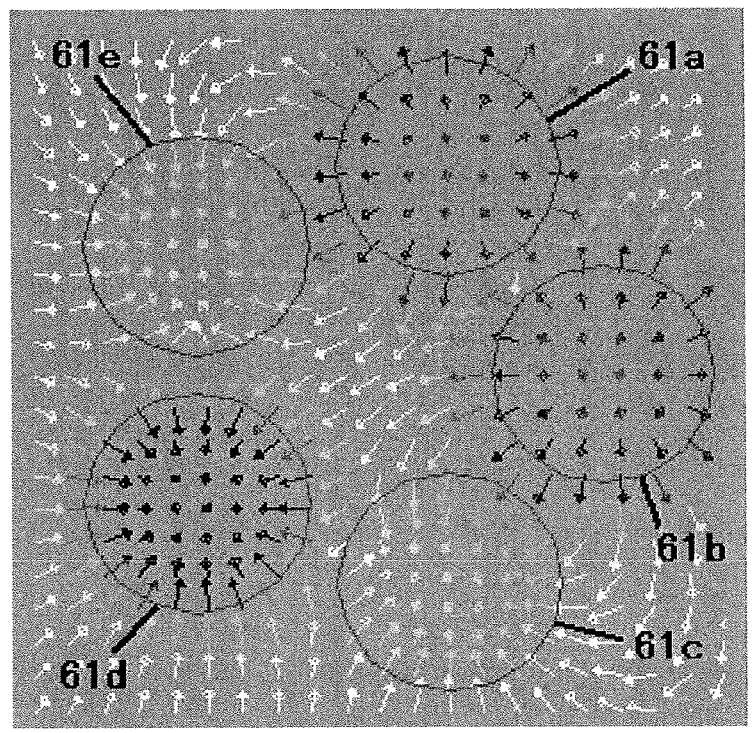
FIG. 7 is a top view showing the directions and the intensities of the magnetic field generated by the eddy current inspection probe at time T/3.
Figure 8:
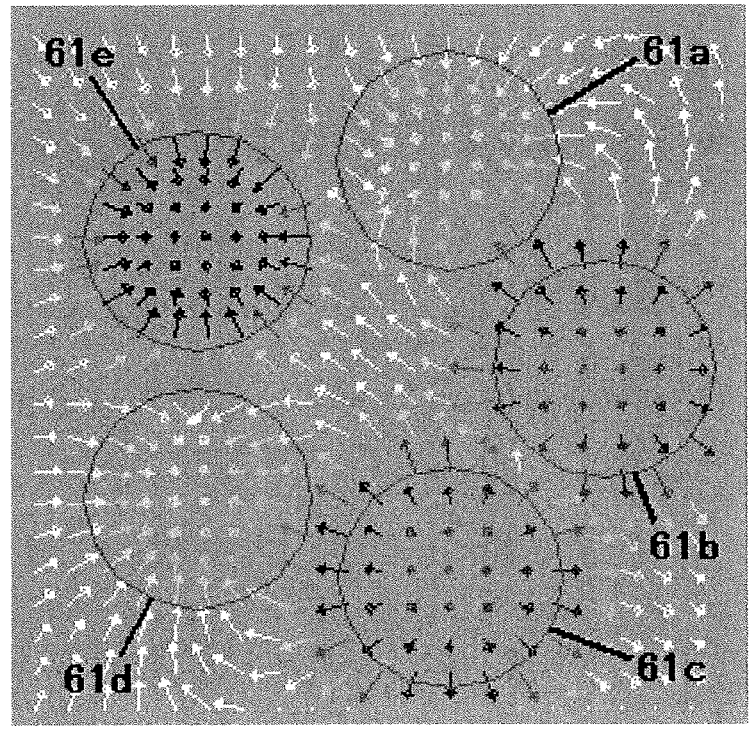
FIG. 8 is a top view showing the directions and the intensities of the magnetic field generated by the eddy current inspection probe at time T/2.
Figure 9:
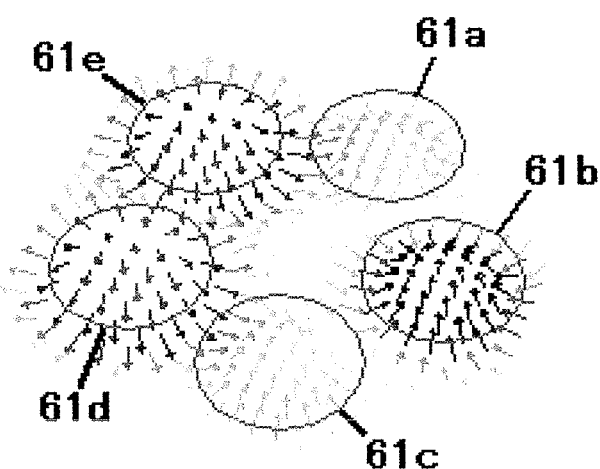
FIG. 9 is a perspective view showing the directions and the intensities of the magnetic field generated by the eddy current inspection probe at time 0.
Figure 10:
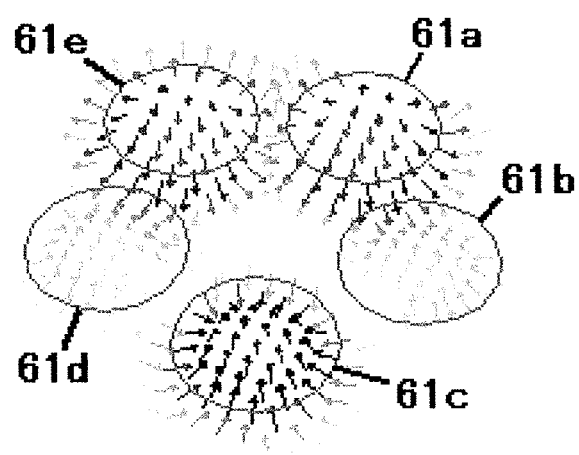
FIG. 10 is a perspective view showing the directions and the intensities of the magnetic field generated by the eddy current inspection probe at time T/6.
Figure 11:
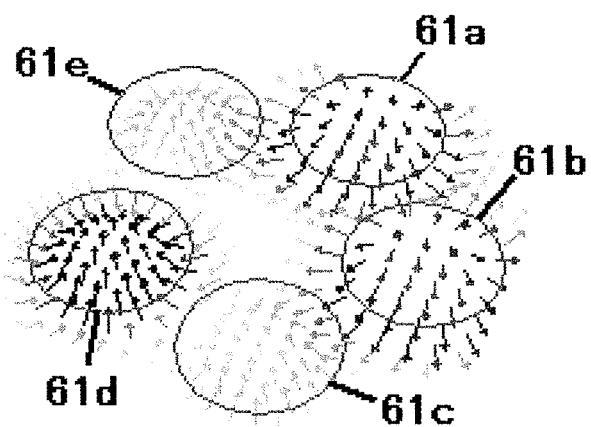
FIG. 11 is a perspective view showing the directions and the intensities of the magnetic field generated by the eddy current inspection probe at time T/3.
Figure 12:
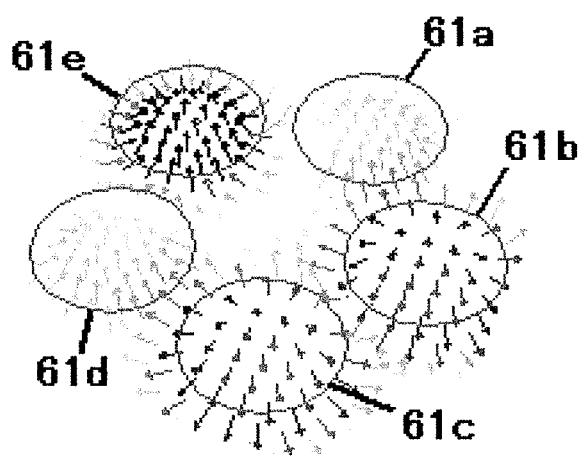
FIG. 12 is a perspective view showing the directions and the intensities of the magnetic field generated by the eddy current inspection probe at time T/2.

FIGS. 5 and 9 show the status of the magnetic field in cases corresponding to the time 0 in FIG. 4. FIGS. 6 and 10 show the status of the magnetic field in cases corresponding to the time T/6 in FIG. 4. FIGS. 7 and 11 correspond to the time T/3 in FIG. 4. FIGS. 8 and 12 correspond to the time T/2 in FIG. 4.

In FIGS. 5 and 9, for example, it is seen that a strong upward magnetic field has occurred in the vicinity of the excitation coil 61b (in which the rate of change of the applied excitation current is high at the time 0) and a strong downward magnetic field has occurred in the vicinity of the excitation coils 61d and 61e (in which the rate of change of the applied excitation current is high in the opposite direction at the time 0). In FIGS. 6 and 10, it is seen that a strong upward magnetic field has occurred in the vicinity of the excitation coil 61c (in which the rate of change of the applied excitation current is high at the time T/6) and a strong downward magnetic field has occurred in the vicinity of the excitation coils 61e and 61a (in which the rate of change of the applied excitation current is high in the opposite direction at the time T/6). Similarly, in FIGS. 7 and 11, it is seen that a strong upward magnetic field has occurred in the vicinity of the excitation coil 61d (in which the rate of change of the applied excitation current is high at the time T/3) and a strong downward magnetic field has occurred in the vicinity of the excitation coils 61a and 61b (in which the rate of change of the applied excitation current is high in the opposite direction at the time T/3). In FIGS. 8 and 12, it is seen that a strong upward magnetic field has occurred in the vicinity of the excitation coil 61e (in which the rate of change of the applied excitation current is high at the time T/2) and a strong downward magnetic field has occurred in the vicinity of the excitation coils 61b and 61c (in which the rate of change of the applied excitation current is high in the opposite direction at the time T/2).

As above, the eddy current inspection probe 6 operates so as to successively generate the magnetic fields in the order of the excitation coils 61a-61e. It is also seen that the magnetic fields in the z direction (vertical direction) are canceled out among the excitation coils 61a-61e and weakened extremely at the center of the excitation coils 61a-61e, that is, at the center of the postulated circumference 64 where the detection coil 62 is placed.

Figure 13:
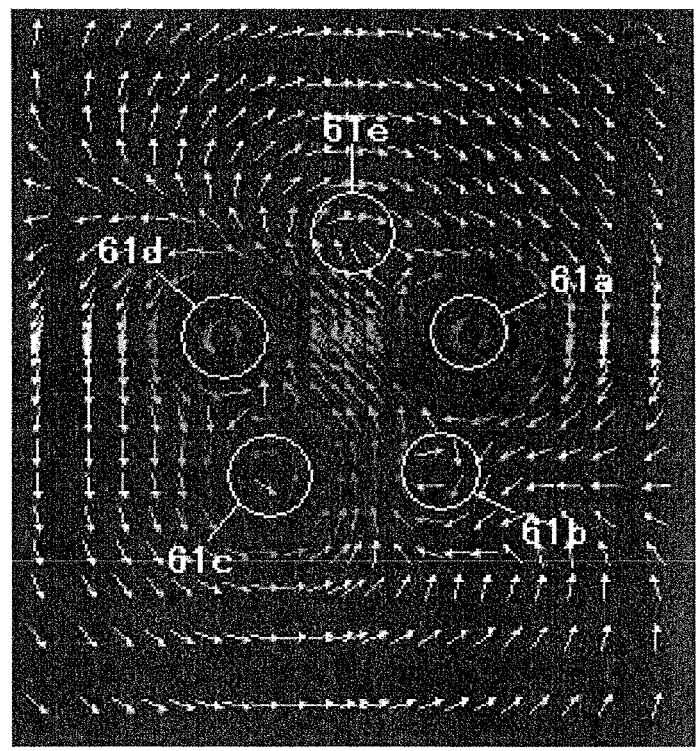
FIG. 13 is a top view showing the directions and the intensities of an eddy current occurring at time 0 in the inspection target placed under the eddy current inspection probe.
Figure 14:
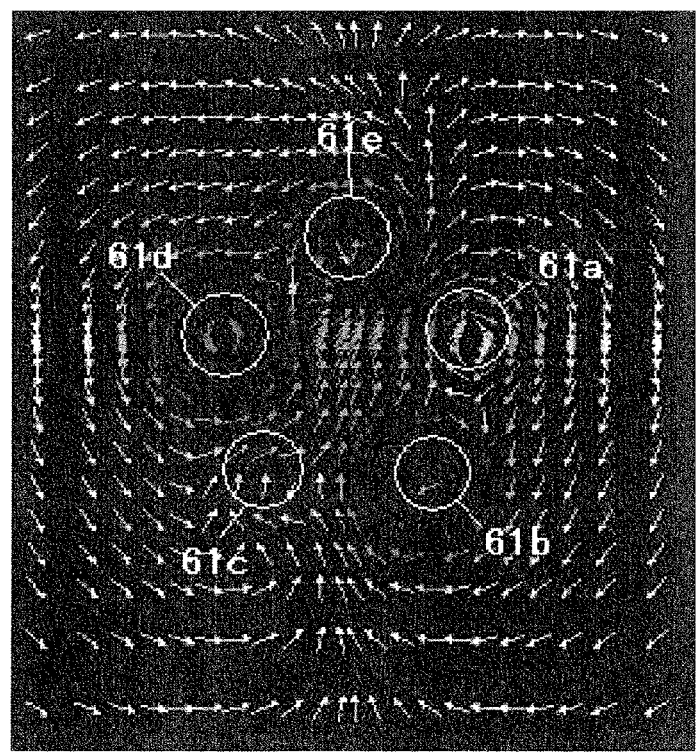
FIG. 14 is a top view showing the directions and the intensities of the eddy current occurring at time T/6 in the inspection target placed under the eddy current inspection probe.
Figure 15:
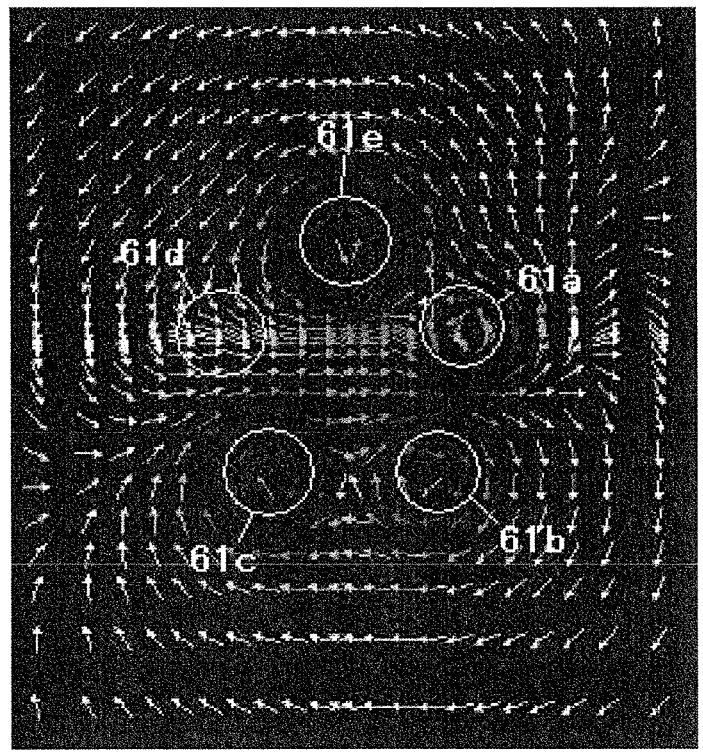
FIG. 15 is a top view showing the directions and the intensities of the eddy current occurring at time T/3 in the inspection target placed under the eddy current inspection probe.
Figure 16:
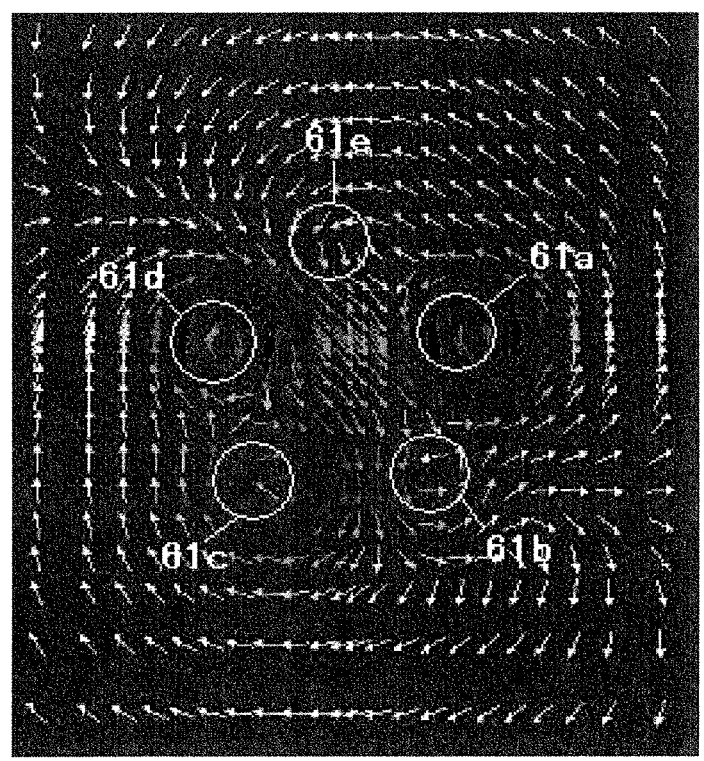
FIG. 16 is a top view showing the directions and the intensities of the eddy current occurring at time T/2 in the inspection target placed under the eddy current inspection probe.

FIGS. 13-16 are schematic diagrams showing the status of the eddy current occurring in the inspection target (test object) placed under the eddy current inspection probe 6 when the magnetic fields shown in FIGS. 5-12 are generated by controlling the excitation currents as shown in FIG. 4. FIG. 13 shows the status of the eddy current in cases corresponding to the time 0 in FIG. 4. FIGS. 14, 15 and 16 show the status of the eddy current in cases corresponding to the time T/6, T/3 and T/2 in FIG. 4, respectively. In the figures, the direction of the eddy current at each position is indicated by the direction of each arrow, and the intensity of the eddy current at each position is indicated by the darkness of each arrow. Each arrow represents a stronger/weaker eddy current with the increase/decrease in the darkness (i.e., with the increase in the blackness/whiteness).

The eddy currents occurring in the test object due to the change in the magnetic fields generated by the excitation coils 61a-61e of the eddy current inspection probe 6 are canceled out in the z direction (vertical direction) similarly to the cancellation of the magnetic fields.

On the other hand, in the directions of the x-y plane (i.e., in the directions along the surface of the test object), a strong eddy current exists at each time point. With the passage of time, that is, with the change in the magnetic fields generated by the excitation coils 61a-61e, the flowing direction of the eddy current changes in a rotational manner. Specifically, in FIG. 13, an eddy current flowing from around the excitation coil 61b in the direction between the excitation coils 61d and 61e has occurred at the time 0. In FIG. 14, an eddy current flowing from around the excitation coil 61c in the direction between the excitation coils 61e and 61a has occurred at the time T/6. Similarly, in FIG. 15, an eddy current flowing from around the excitation coil 61d in the direction of the excitation coil 61a has occurred at the time T/3. In FIG. 16, an eddy current flowing from around the midpoint between the excitation coils 61d and 61e in the direction of the excitation coil 61b has occurred at the time T/2.

Here, the variation in the intensity of the eddy current in the depth direction of the test object (z direction) will be explained referring to FIG. 17.

Figure 17:
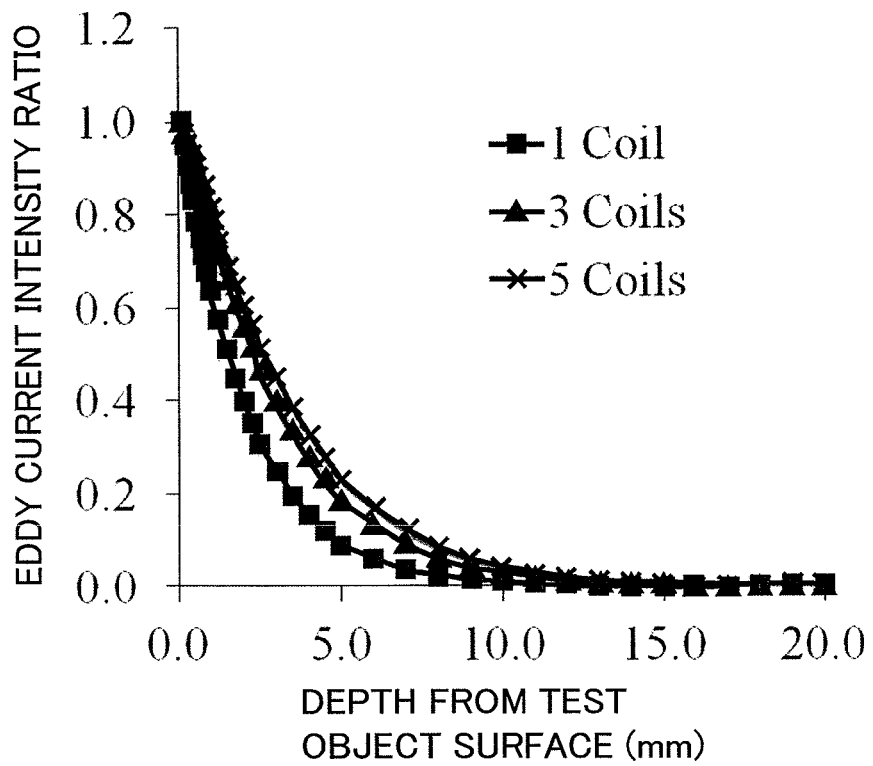
FIG. 17 is a graph showing the relationship between the eddy current intensity and the depth from the surface of the test object (inspection target).

FIG. 17 is a graph showing the relationship between the eddy current intensity and the depth from the surface of the test object, wherein the horizontal axis represents the depth from the test object surface and the vertical axis represents eddy current intensity ratio determined by normalizing the eddy current intensity so that the intensity at the test object surface equals 1. In FIG. 17, the eddy current intensity under the center of the postulated circumference 64 is shown and compared among cases where the number of excitation coils arranged on the postulated circumference 64 is one, three and five. As shown in FIG. 17, the drop in the eddy current intensity ratio with the increase in the depth from the test object surface is smaller in the case where the number of excitation coils is three compared to the case where the number is one. The drop in the eddy current intensity ratio with the increase in the depth is still smaller in the case where the number of excitation coils is five. The difference between the case with five excitation coils and the case with three excitation coils is smaller than the difference between the case with three excitation coils and the case with one excitation coil. Therefore, it can be presumed that using approximately five or seven excitation coils for the eddy current inspection probe 6 is the most cost effective.

Next, the eddy current inspection executed by the eddy current inspection device and the eddy current inspection probe 6 configured as above will be explained below. This explanation will be given of a case where an experimental test object having defects artificially formed from the test object's back side (artificial defects) is used.

Figure 18:
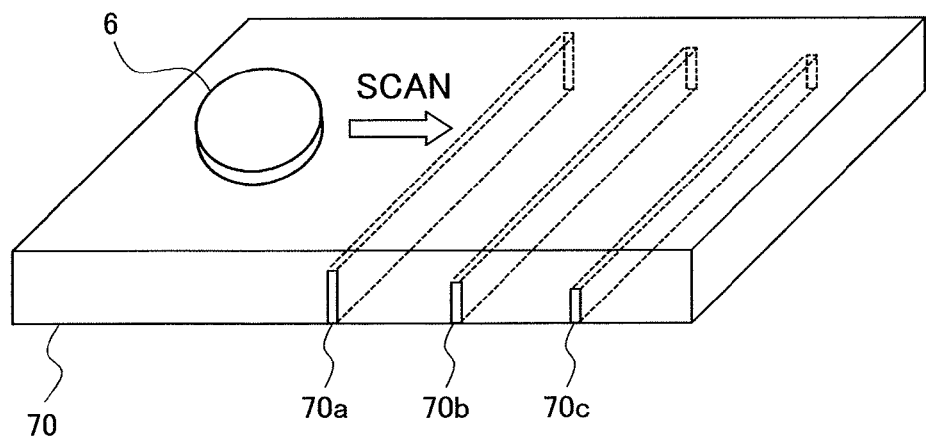
FIG. 18 is a perspective view schematically showing the scanning of the test object by the eddy current inspection probe.
Figure 19:
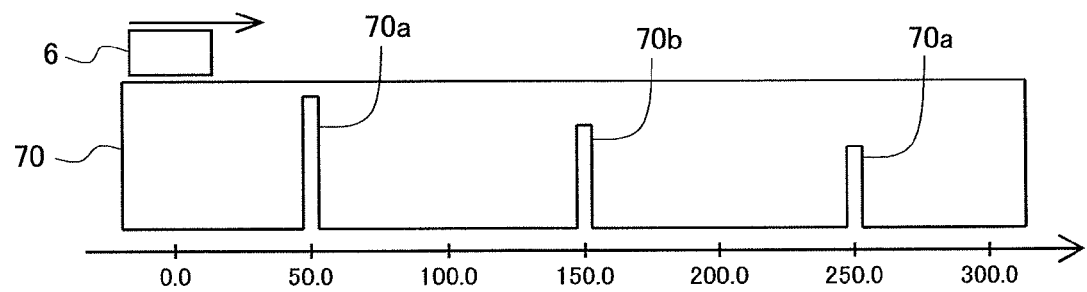
FIG. 19 is a vertical sectional view schematically showing the scanning of the test object by the eddy current inspection probe.

FIGS. 18 and 19 are diagrams schematically showing the scanning of the test object by the eddy current inspection probe, wherein FIG. 18 is a perspective view and FIG. 19 is a vertical sectional view.

As shown in FIGS. 18 and 19, the test object 70 has artificial defects 70a-70c formed from the back side. The artificial defects 70a-70c have been formed to differ from one another in the depth from the surface of the test object. The artificial defect 70a is the shallowest from the surface, the artificial defect 70b is at an intermediate depth, and the artificial defect 70c is the deepest from the surface. The artificial defects 70a, 70b and 70c have been formed to be arranged in this order in the scanning direction of the eddy current inspection probe 6. Thus, the eddy current inspection probe 6 is scanned over the artificial defects to successively cross the artificial defects 70a, 70b and 70c in this order.

Figure 20:
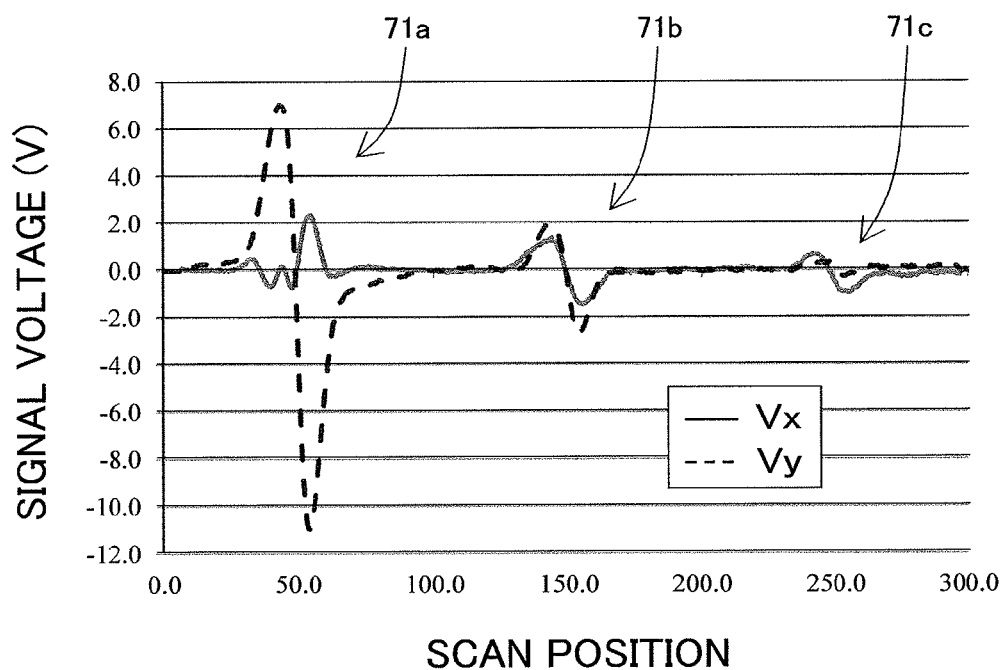
FIG. 20 is a graph showing the correspondence between the scan position and the real number component and the imaginary number component of detected signal voltage.
Figure 21:
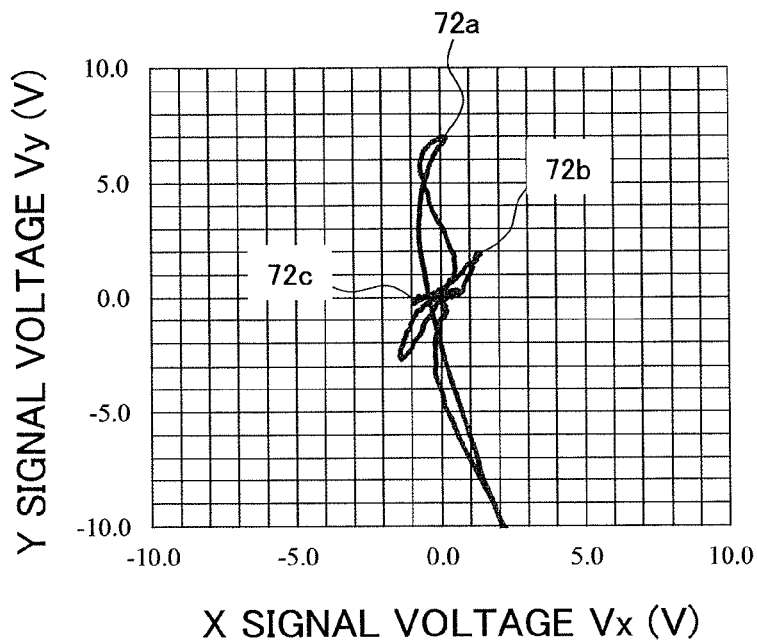
FIG. 21 is a graph showing the real number component and the imaginary number component of the detected signal voltage as a Lissajou's figure.

FIGS. 20 and 21 show results of calculation by the magnetic field distribution evaluating unit 51 in regard to the result of the detection by the magnetic field detecting element 62 when the test object is scanned by the eddy current inspection probe. FIG. 20 is a graph showing the correspondence between the scan position and the real number component (Vx) and the imaginary number component (Vy) of the detected signal voltage. FIG. 21 is a graph showing the detected signal voltage as a Lissajou's figure having the horizontal axis representing the real number component (Vx) and the vertical axis representing the imaginary number component (Vy).

As shown in FIG. 20, in the scan of the test object by the eddy current inspection probe 6, both the real number component (Vx) and the imaginary number component (Vy) of the detected signal voltage are substantially 0 at positions other than the artificial defects, that is, at positions with no defect. Therefore, also in the Lissajou's figure of FIG. 21, the detected signal voltages are drawn almost exclusively at the central point (where both the real number component (Vx) and the imaginary number component (Vy) equal 0).

In cases where the magnetic field detecting element 62 passes over the artificial defect 70a, 70b or 70c in the scan of the test object by the eddy current inspection probe 6, both the real number component (Vx) and the imaginary number component (Vy) change corresponding to each artificial defect 70a, 70b, 70c as indicated by the changing parts 71a, 71b and 71c of the detected signal voltage shown in FIG. 20. Also in the Lissajou's figure of FIG. 21, changes 72a, 72b and 72c in the drawing appear corresponding to the artificial defects 70a, 70b and 70c, respectively.

Figure 22:
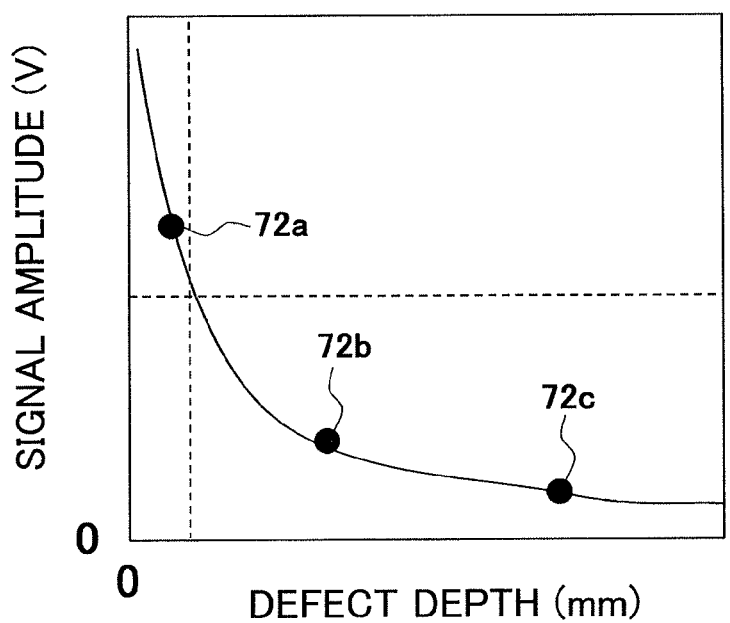
FIG. 22 is a graph showing a calibration curve in regard to the defect depth and the amplitude of the detected signal.

In order to detect the presence/absence of a defect inside the surface of the actual test object and measure the depth of each defect based on the above detection result, a calibration curve in regard to the defect depth and the amplitude of the detected signal is generated as shown in FIG. 22 from the result of the measurement of the artificial defects 70a-70c. The presence/absence of a defect and the depth of each defect are measured by estimation by comparing the result of detection of the actual test object with the calibration curve.

Effects achieved by this embodiment configure as above will be described below.

Defects in the test object can develop not only at the surface of the test object or in the vicinity of the surface but also in a deeper part of the test object. Therefore, defect inspection in deeper parts of test objects is being required in order to further improve the reliability of the defect inspection of test objects.

The eddy current in the test object caused by the magnetic fluxes from the excitation coils has the tendency to develop to a deeper part of the test object with the decrease in the frequency of the excitation currents. The measurable range of the characteristic change of the test object in the depth direction is determined as a skin depth δ(m) by use of the following expression (1):

$$\delta = (\pi f \sigma \mu)^{(-1/2)} \quad (1)$$

Since the conductivity σ and the magnetic permeability μ of the test object are fixed values in the above expression (1), it can be understood that the skin depth δ increases with the decrease in the frequency f. The skin depth δ represents the depth at which the eddy current intensity equals 1/e of the eddy current intensity at the surface of the test object (e: the base of natural logarithms (=2.73 . . . )).

However, there exists the problem that the magnetic field information acquired from the deep part of the test object is far more deficient compared to the magnetic field information from around the surface of the test object even at still lower frequencies. Therefore, the defect inspection in deep parts of test objects has been extremely difficult.

In contrast, in this embodiment, three or more odd number of (five in this embodiment) excitation coils are arranged at even intervals in the circumferential direction on a postulated circumference. The excitation currents applied to the excitation coils are controlled so that the phase difference between excitation currents applied to adjacent ones of the excitation coils arranged in the circumferential direction on the postulated circumference equals one cycle divided by the number of excitation coils. The magnetic field generated according to the eddy current occurring in the test object due to the magnetic field caused by the application of the excitation currents to the excitation coils is detected by a detector arranged on a postulated plane containing the postulated circumference but inside the postulated circumference. With this configuration, defects existing in deeper parts of test objects can be detected.

Further, the eddy current inspection device is configured to detect the defects inside the surface of the test object by use of a rotational magnetic field and rotational eddy current. Therefore, high detectivity independent of the direction of each defect can be achieved.

Incidentally, while five excitation coils 61a-61e are arranged at even intervals in the circumferential direction on the postulated circumference 64 and the detection coil 62 is arranged at the center of the postulated circumference 64 on the postulated plane 63 in this embodiment, the detection coil 62 may also be arranged at a position inside the postulated circumference 64 and shifted from the center.

Second Embodiment

A second embodiment of the present invention will be described below with reference to figures.

In this embodiment, the excitation signal generating section in the first embodiment is configured in multistage structure.

Figure 23:
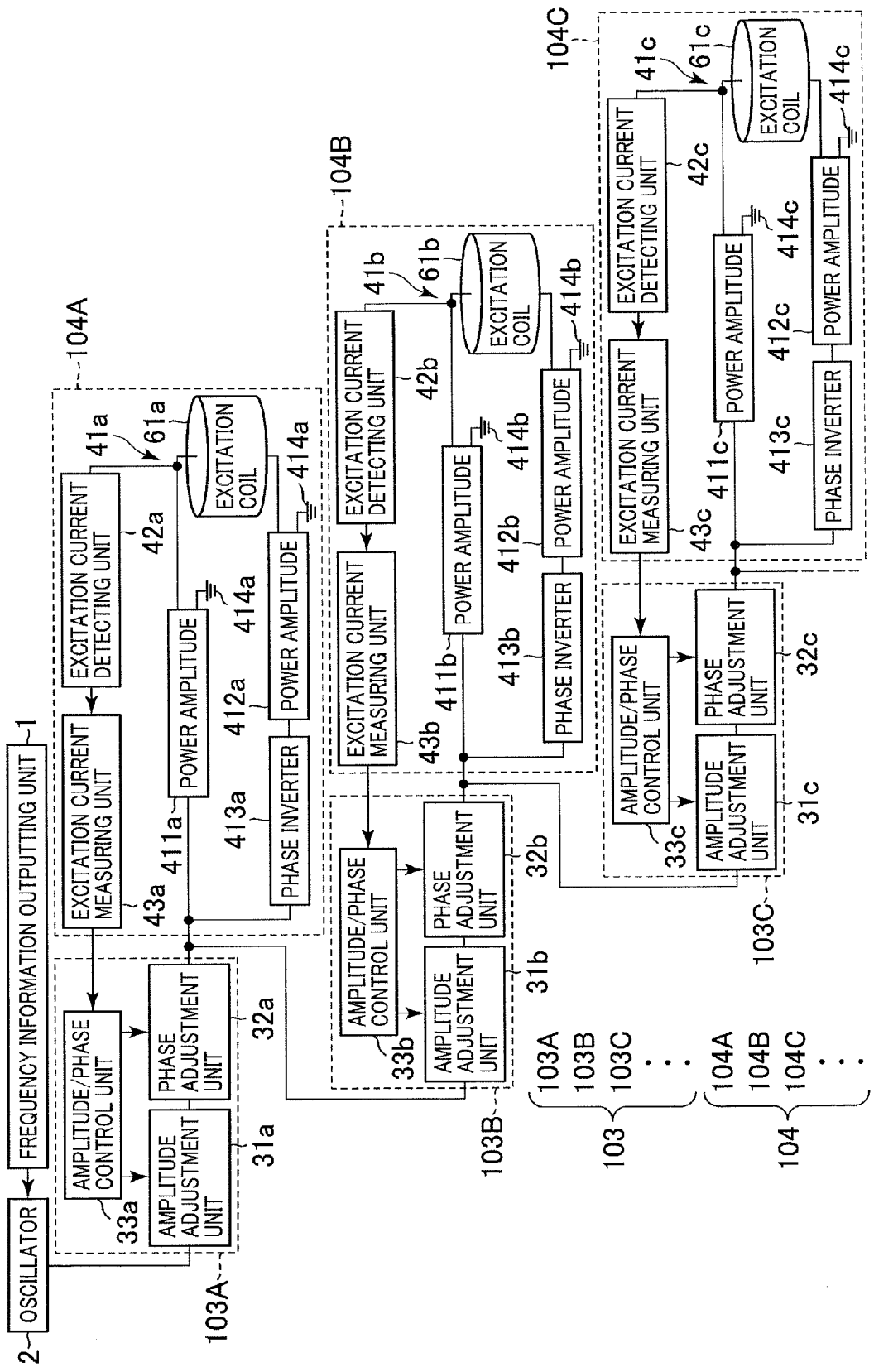
FIG. 23 is a functional block diagram schematically showing principal parts of the configuration of an eddy current inspection device in accordance with a second embodiment of the present invention.

FIG. 23 is a functional block diagram showing the outline of the excitation signal generating section, the magnetic field generating section and the excitation coils of the eddy current inspection device in accordance with this embodiment. Illustration and explanation of components corresponding to the detection section in the first embodiment are omitted for brevity. Components in FIG. 23 equivalent to those in the first embodiment are assigned the same reference characters as in the first embodiment and repeated explanation thereof is omitted here.

As partially shown in FIG. 23, the eddy current inspection device of this embodiment comprises a frequency information outputting unit 1, a fundamental signal generating section 7, excitation signal generating units 103A, 103B, 103C, . . . , magnetic field generating units 104A, 104B, 104C, and a detection section 5. The frequency information outputting unit 1 generates and outputs information on the frequency of the fundamental signal. The fundamental signal generating section 7 has an oscillator 2 for generating and outputting the fundamental signal (as the foundation for generating the excitation currents to be used for the inspection of the test object) based on the frequency information supplied from the frequency information outputting unit 1. The excitation signal generating unit 103A generates and outputs an excitation signal based on the fundamental signal supplied from the oscillator 2. The excitation signal generating unit 103B generates and outputs an excitation signal based on the output signal from the excitation signal generating unit 103A. The excitation signal generating unit 103C generates and outputs an excitation signal based on the output signal from the excitation signal generating unit 103B. The other excitation signal generating units (not shown) also generate and output excitation signals based on the output signal from the excitation signal generating unit 103C. The magnetic field generating unit 104A generates a magnetic field to be used for the inspection according to the excitation signal supplied from the excitation signal generating unit 103A. The magnetic field generating unit 104B generates a magnetic field to be used for the inspection according to the excitation signal supplied from the excitation signal generating unit 103B. The magnetic field generating unit 104C generates a magnetic field to be used for the inspection according to the excitation signal supplied from the excitation signal generating unit 103C. The other magnetic field generating units (not shown) also generate magnetic fields to be used for the inspection according to the excitation signals supplied from the corresponding excitation signal generating units, respectively. The detection section 5 (see FIG. 1) detects a magnetic field generated according to an eddy current occurring in the test object due to the magnetic fields generated by the magnetic field generating units 104A, 104B, 104C, . . . .

The excitation signal generating units 103A, 103B, 103C, . . . form an excitation signal generating section 103 which generates and outputs the excitation signals based on the fundamental signal supplied from the oscillator 2. The magnetic field generating units 104A, 104B, 104C, . . . form a magnetic field generating section 104 which generates the magnetic fields to be used for the inspection according to the excitation signals supplied from the excitation signal generating section 103. Among the excitation signal generating units 103A, 103B, 103C, . . . and the magnetic field generating units 104A, 104B, 104C, . . . , only those corresponding to the excitation coils 61a-61c are shown in FIG. 23 as representatives.

The excitation signal generating unit 103A includes an amplitude adjustment unit 31a which adjusts the amplitude of the fundamental signal supplied from the oscillator 2, a phase adjustment unit 32a which adjusts the phase of the fundamental signal and outputs the adjusted signal as the excitation signal, and an amplitude/phase control unit 33a which controls the operation of the amplitude adjustment unit 31a and the phase adjustment unit 32a based on a measurement result inputted from an excitation current measuring unit 43a.

Each excitation signal generating unit 103B, 103C, . . . includes an amplitude adjustment unit 31b, 31c, . . . which receives the excitation signal from the prior excitation signal generating unit 103A, 103B, . . . as a fundamental signal and adjusts the amplitude of the fundamental signal, a phase adjustment unit 32b, 32c, . . . which adjusts the phase of the fundamental signal and outputs the adjusted signal as the excitation signal, and an amplitude/phase control unit 33b, 33c, . . . which controls the operation of the amplitude adjustment unit 31b, 31c, . . . and the phase adjustment unit 32b, 32c, . . . based on an excitation current measurement result inputted from an excitation current measuring unit 43b, 43c, . . . .

The magnetic field generating unit 104A includes the excitation coil 61a, power amplifiers 411a and 412a, a phase inverter 413a, an excitation current detecting unit 42a, and an excitation current measuring unit 43a. The excitation coil 61a generates a magnetic field according to an excitation current supplied thereto. The power amplifier 411a amplifies the electric power of the excitation signal supplied from the excitation signal generating unit 103A and applies the amplified electric power to one end (normal phase side) of the excitation coil 61a as an excitation signal. The phase inverter 413a inverts the phase of the excitation signal supplied from the excitation signal generating unit 103A. The power amplifier 412a amplifies the electric power of the excitation signal supplied from the phase inverter 413a and applies the amplified electric power to the other end (reverse phase side) of the excitation coil 61a as another excitation signal. The excitation current detecting unit 42a detects the amplitude component and the phase component of the excitation current applied by the power amplifier 411a to the normal phase side of the excitation coil 61a. The excitation current measuring unit 43a measures the amplitude and the phase of the excitation current based on the result of the detection by the excitation current detecting unit 42a and outputs the excitation current measurement result to the amplitude/phase control unit 33a of the excitation signal generating unit 103A.

The other magnetic field generating units 104B, 104C, . . . also have equivalent configurations. Specifically, each magnetic field generating unit 104B, 104C, . . . includes an excitation coil 61b, 61c . . . which generates a magnetic field according to the excitation current supplied thereto, a power amplifier 411b, 411c, . . . which amplifies the electric power of the excitation signal supplied from the excitation signal generating unit 103B, 103C, . . . and applies the amplified electric power to one end (normal phase side) of the excitation coil 61b, 61c, . . . as an excitation signal, a phase inverter 413b, 413c, . . . which inverts the phase of the excitation signal supplied from the excitation signal generating unit 103B, 103C, . . . , a power amplifier 412b, 412c, . . . which amplifies the electric power of the excitation signal supplied from the phase inverter 413b, 413c, . . . and applies the amplified electric power to the other end (reverse phase side) of the excitation coil 61b, 61c, . . . as another excitation signal, an excitation current detecting unit 42b, 42c, . . . which detects the amplitude component and the phase component of the excitation current applied by the power amplifier 411b, 411c, . . . , to the normal phase side of the excitation coil 61b, 61c, . . . , and an excitation current measuring unit 43b, 43c, . . . , which measures the amplitude and the phase of the excitation current based on the result of the detection by the excitation current detecting unit 42b, 42c, . . . and outputs the excitation current measurement result to the amplitude/phase control unit 33b, 33c, . . . of the excitation signal generating unit 103B, 103C, . . . .

In this embodiment, the excitation current (excitation signals) is applied to both ends of each excitation coil 61a, 61b, 61c, . . . as differential input by the power amplifier 411a, 411b, 411c, . . . , the power amplifier 412a, 412b, 412c, . . . and the phase inverter 413a, 413b, 413c, . . . . Since the grounding of one end is made unnecessary in this configuration, fluctuation in the grounding potential occurring when the electric current value fluctuates due to impedance fluctuation of the excitation coil 61a, 61b, 61c, . . . can be suppressed. This configuration forms an interference avoidance function of preventing the interference among the magnetic field generating units 104A, 104B, 104C, . . . .

The other configuration is equivalent to that in the first embodiment.

Also with this embodiment configured as above, effects similar to those of the first embodiment can be achieved.

Third Embodiment

A third embodiment of the present invention will be described below with reference to figures.

In this embodiment, the excitation current generating section in the first embodiment is provided integrally with the eddy current inspection probe 6.

Figure 24:
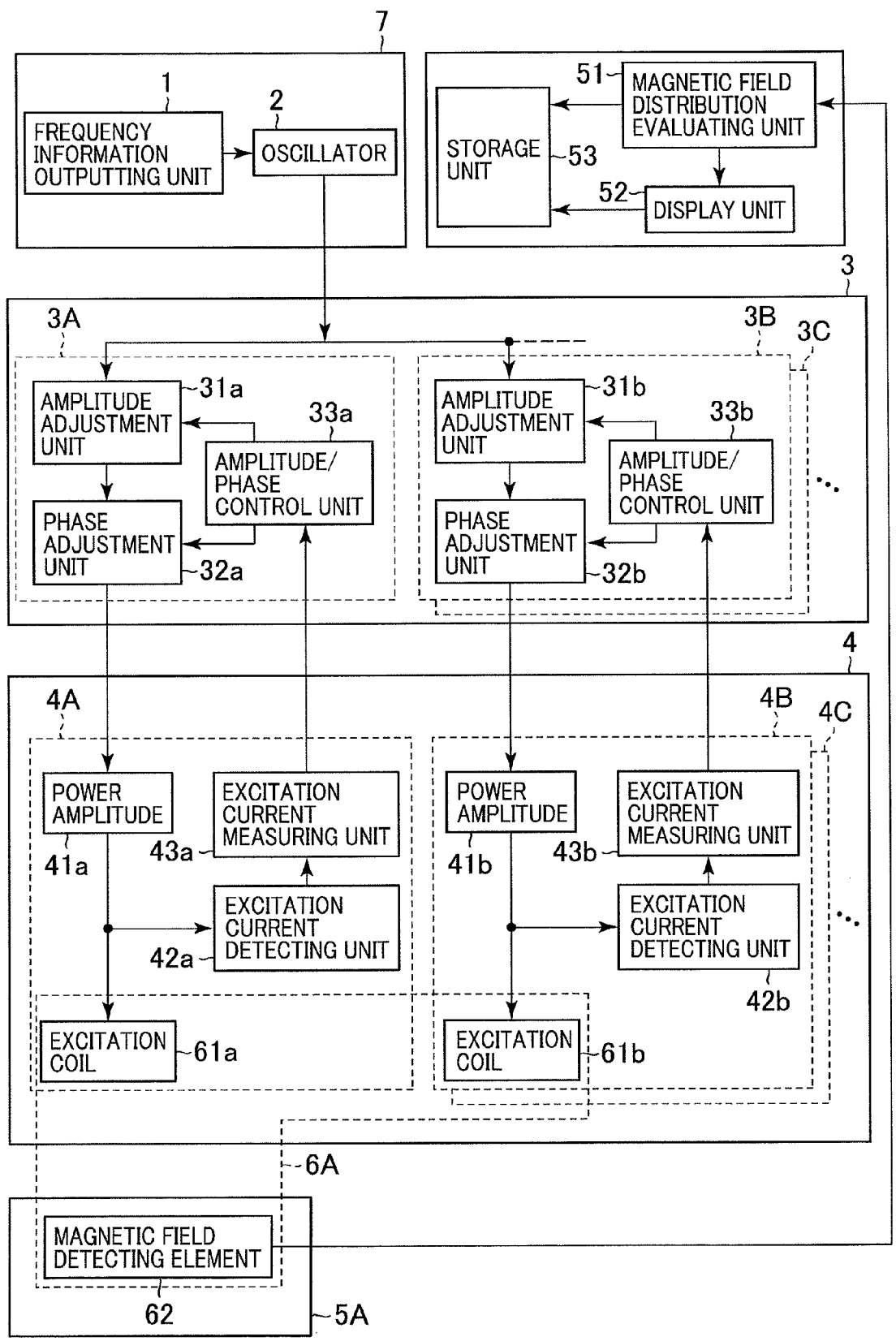
FIG. 24 is a functional block diagram showing the outline of the overall configuration of an eddy current inspection device in accordance with a third embodiment of the present invention.

FIG. 24 is a functional block diagram schematically showing the overall configuration of an eddy current inspection device in accordance with this embodiment. Components in FIG. 24 equivalent to those in the first embodiment are assigned the same reference characters as in the first embodiment and repeated explanation thereof is omitted for brevity.

In FIG. 24, the eddy current inspection device of this embodiment comprises a frequency information outputting unit 1, a fundamental signal generating section 7, an excitation signal generating section 3, a magnetic field generating section 4, a detection section 5A, and a detection result evaluating unit 8. The frequency information outputting unit 1 generates and outputs information on the frequency of the fundamental signal. The fundamental signal generating section 7 has an oscillator 2 for generating and outputting the fundamental signal (as the foundation for generating excitation currents to be used for the inspection of the test object) based on the frequency information supplied from the frequency information outputting unit 1. The excitation signal generating section 3 generates and outputs excitation signals based on the fundamental signal supplied from the oscillator 2. The magnetic field generating section 4 generates a magnetic field to be used for the inspection according to the excitation signals supplied from the excitation signal generating section 3. The detection section 5A detects a magnetic field generated according to an eddy current occurring in the test object due to the magnetic field generated by the magnetic field generating section 4. The detection result evaluating unit 8 evaluates and stores the result of the magnetic field detection by the detection section 5A.

The other configuration is equivalent to that in the first embodiment.

In the configuration described above, the fundamental signal generating section 7 and the detection result evaluating unit 8 form a main unit. The excitation signal generating section 3 and the power amplifiers 41a-41c, . . . , the excitation current detecting units 42a-42c, . . . and the excitation current measuring units 43a-43c, . . . of the magnetic field generating section 4 form an excitation current generating section which generates the excitation currents according to the fundamental signal. The excitation coils 61a-61c, . . . and the magnetic field detecting element 62 form a sensor unit 6A. The sensor unit 6A and the detection section 5A having the magnetic field detecting element 62 form an eddy current inspection probe which is provided separately from the main unit to be able to scan the test object while moving along the surface of the test object.

Also with this embodiment configured as above, effects similar to those of the first embodiment can be achieved.

What is claimed is:

1. An eddy current inspection device comprising:
a main unit which has a function of generating and outputting a fundamental signal as the foundation for generating excitation currents to be used for inspection of a test object;
an eddy current inspection probe which is provided separately from the main unit to be able to scan the test object while moving along the surface of the test object, the eddy current inspection probe including three or more odd number of excitation coils which are arranged at even intervals in a circumferential direction on a postulated circumference to be excited by the excitation currents applied thereto and a detector which is arranged on a postulated plane containing the postulated circumference but inside the postulated circumference to detect a magnetic field generated according to an eddy current occurring in the test object due to a magnetic field caused by the application of the excitation currents to the excitation coils; and
a plurality of excitation current generators, including a first excitation current generator that generates and outputs a first excitation current of the excitation currents based on the fundamental signal, a second excitation current generator that generates and outputs a second excitation current of the excitation currents based on an output of the first excitation current generator, and one or more odd number of other excitation current generators, each of which generates and outputs another excitation current of the excitation currents based on an output of a previous adjacent one of the other excitation current generators, so that the phase difference between excitation currents applied to adjacent ones of the excitation coils arranged in the circumferential direction on the postulated circumference in the eddy current inspection probe equals one cycle divided by the number of excitation coils;
wherein the detector of the eddy current inspection probe is arranged at a position inside the postulated circumference.

2. An eddy current inspection probe comprising:
a detection function unit including three or more odd number of excitation coils which are arranged at even intervals in a circumferential direction on a postulated circumference to be excited by excitation currents applied thereto and a detector which is arranged on a postulated plane containing the postulated circumference but inside the postulated circumference to detect a magnetic field generated according to an eddy current occurring in a test object due to a magnetic field caused by the application of the excitation currents to the excitation coils; and
a plurality of excitation current generators, including a first excitation current generator that generates and outputs a first excitation current of the excitation currents based on a fundamental signal supplied from a main unit having a function of outputting the fundamental signal as the foundation for generating the excitation currents to be used for inspection of the test object, a second excitation current generator that generates and outputs a second excitation current of the excitation currents based on an output of the first excitation current generator, and one or more odd number of other excitation current generators, each of which generates and outputs another excitation current of the excitation currents based on an output of a previous adjacent one of the other excitation current generators, so that the phase difference between excitation currents applied to adjacent ones of the excitation coils arranged in the circumferential direction on the postulated circumference in the eddy current inspection probe equals one cycle divided by the number of excitation coils;
wherein the detector is arranged at a position inside the postulated circumference.

3. An eddy current inspection probe comprising a detection function unit which includes:
three or more odd number of excitation coils which are arranged at even intervals in a circumferential direction on a postulated circumference to be excited by excitation currents applied thereto; and
a detector which is arranged on a postulated plane containing the postulated circumference but inside the postulated circumference to detect a magnetic field generated according to an eddy current occurring in a test object due to a magnetic field caused by the application of the excitation currents to the excitation coils, wherein:
the excitation coils are supplied with excitation currents generated from a plurality of excitation current generators, including a first excitation current generator that generates and outputs a first excitation current of the excitation currents based on a fundamental signal, a second excitation current generator that generates and outputs a second excitation current of the excitation currents based on an output of the first excitation current generator, and one or more odd number of other excitation current generators, each of which generates and outputs another excitation current of the excitation currents based on an output of a previous adjacent one of the other excitation current generators, so that the phase difference between excitation currents applied to adjacent ones of the excitation coils arranged in the circumferential direction on the postulated circumference in the eddy current inspection probe equals one cycle divided by the number of excitation coils based on the fundamental signal supplied from a main unit having a function of outputting the fundamental signal as the foundation for generating the excitation currents to be used for inspection of the test object; and
wherein the detector is arranged at a position inside the postulated circumference.

* * * * *